United States Patent [19]

Kaye

[11] 4,437,763

[45] Mar. 20, 1984

[54] CONTROL OF DETECTOR GAIN HYSTERESIS IN A SINGLE BEAM SPECTROPHOTOMETER

[75] Inventor: Wilbur I. Kaye, Corona del Mar, Calif.

[73] Assignee: Beckman Instruments, Inc., Fullerton, Calif.

[21] Appl. No.: 335,021

[22] Filed: Dec. 28, 1981

[51] Int. Cl.³ .......................... G01J 3/00; H01J 40/00
[52] U.S. Cl. ..................................... 356/326; 250/207
[58] Field of Search ................. 356/319, 326; 250/207

[56] References Cited

U.S. PATENT DOCUMENTS 4,367,404 1/1983 Kaye .................................. 250/207

Primary Examiner—Vincent P. McGraw
Attorney, Agent, or Firm—R. J. Steinmeyer; R. R. Meads; J. R. Shewmaker

[57] ABSTRACT

Gain hysteresis exhibited by the photomultiplier detector of a single beam spectrophotometer is reduced by illuminating the detector and applying dynode voltage thereto during the normal "off" or "idle" interval of the spectrophotometer.

3 Claims, 1 Drawing Figure

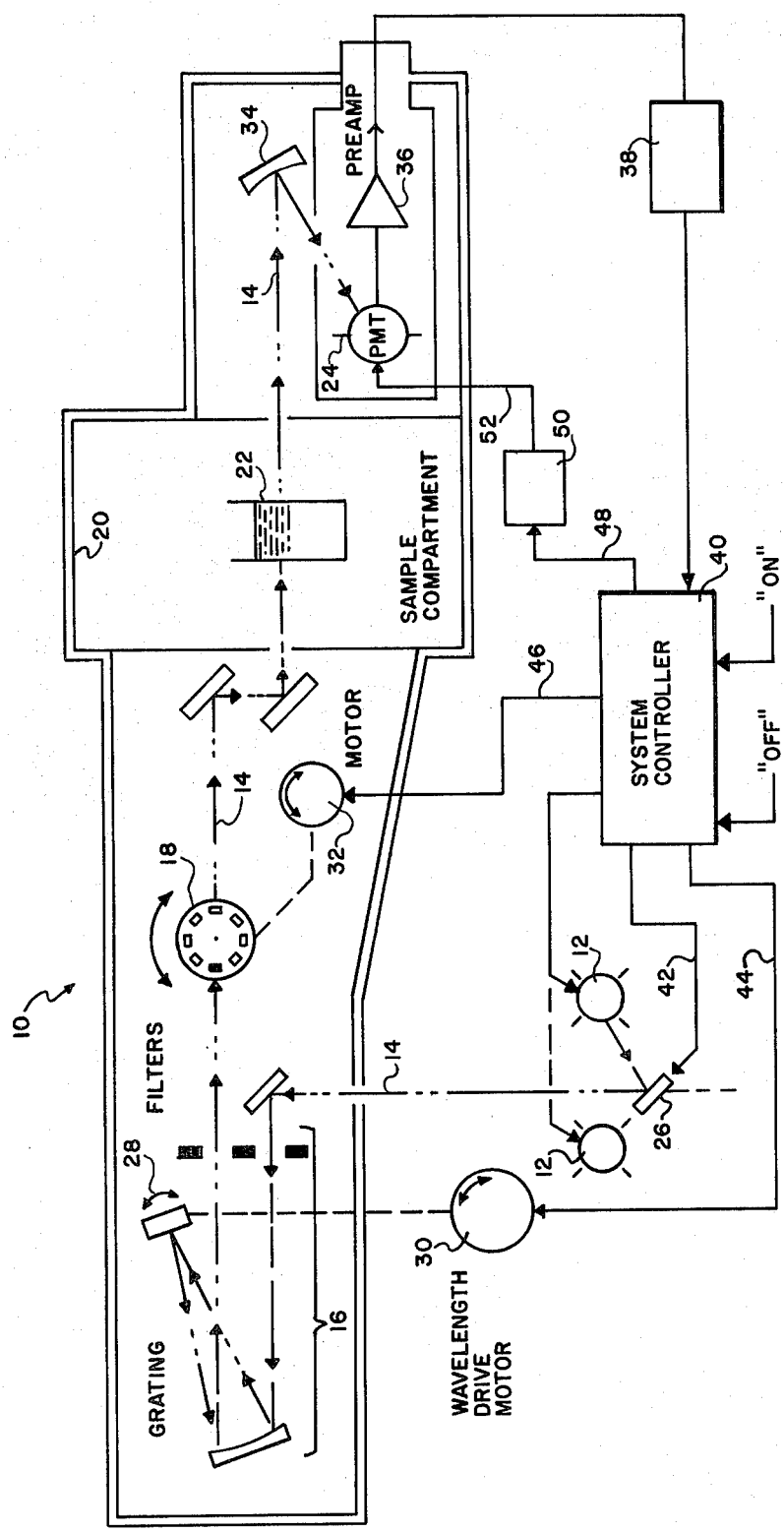

CONTROL OF DETECTOR GAIN HYSTERESIS IN A SINGLE BEAM SPECTROPHOTOMETER

BACKGROUND OF THE INVENTION

1. Field of the Invention

The present invention relates to single beam spectrophotometers and, more particularly, to the control of detector hysteresis in a single beam spectrophotometer.

2. Description of the Prior Art

In a spectrophotometer a sample to be measured is positioned in a light beam and light transmitted, scattered, or otherwise passed or radiated by the sample is directed to a light detector, such as a photomultiplier detector (PMT), which generates an output current signal proportional to the intensity of the detected light. In a photomultiplier detector light flux impinging on a photo-emissive cathode is converted into electrons released from the cathode. The electrons are directed at and cascade down a series of dynodes at each of which the number of electrons increases by a process called secondary emission. The multiplied number of electrons is ultimately collected at an anode and is measured as electrical current. A photomultiplier is a very sensitive light detector since the gain or ratio of anode current to cathode current may be as high as $10^8$ or more.

A serious problem encountered in photomultiplier detectors is output current variation or hystersis causing corresponding nonlinearity in the detector output current with time. Investigation has uncovered several types of such hysteresis variously termed charge hysteresis, dielectric hysteresis, and leakage hysteresis. Charge hysteresis is defined as a variation in gain of a PMT (at constant cathode potential) caused by electrostatic charges developed on insulators proximate the detector dynodes. Dielectric hysteresis is defined as a variation in polarization at different potentials of any dielectric (insulation) separating conductors of the detector. It is manifested when dynode voltage changes. Leakage hysteresis is defined as the variation in resistance between the dynode and anode elements in a PMT. In addition to hysteresis as aforedescribed such detectors are also subject to fatigue which is defined as a slow loss of the secondary electron emission property of dynodes produced when the dynodes are subject to high levels of electron bombardment.

In any event, the problem of photomultiplier hysteresis has long plagued the field of spectrophotometry. Basically many spectrophotometers employ a photomultiplier to measure the extent to which light is transmitted through or absorbed by a sample material of unknown characteristics. This measurement is compared with corresponding transmittance or absorbance measurement of a reference material of known characteristics. Spectrophotometers for this purpose can be broadly categorized as double beam or single beam in design and operation. In a double beam spectrophotometer the sample material and the reference material are measured in rapid sequence in separate optical paths. The beams of light passing through the sample and through the reference are combined spatially into a common beam and this beam is passed to a single photomultiplier detector. The detector output is demodulated to derive signals indicative of the sample and the reference. Fortunately, in a double beam instrument the time constant for detector hysteresis is usually long relative to the time lapse between the sample and reference measurements. Consequently, detector gain varies little between sample and reference measurements and linearity is preserved.

In a single beam spectrophotometer, on the other hand, the sample and the reference are measured at different times in the same optical path. As a result, a single beam instrument is particularly vulnerable to detector hysteresis since hysteresis alone will cause the detector output current to change with time and light level introducing nonlinearity in the detector output. In this regard the sample and reference measurements are typically made approximately one minute apart. Moreover, in scanning operations, if a sample is measured at different wavelength settings across a wavelength interval, the time between sample and reference measurements can be about five minutes or more. During these time intervals detector hysteresis changes the detector output introducing the aforementioned nonlinearity.

Numerous efforts have been made in photomultiplier design and operation to overcome the hysteresis problem. These efforts have met with some degree of success in that detectors are now commercially available exhibiting a reduction in some hysteresis characteristics.

In spite of these recent advances, however, a heretofore unreported type of photomultiplier hysteresis has been discovered which will be termed "gain hysteresis" hereinafter. In this regard it has been discovered that when a photomultiplier detector is exposed to light with dynode voltage applied the detector exhibits a slow reversible change in gain after such exposure. This effect differs from the previously mentioned charge hysteresis in having a much longer time constant, typically thirty minutes. Moreover it may increase with dynode voltage. It differs from previously mentioned fatigue in that gain may either increase or decrease after light exposure. Moreover it occurs at lower anode currents than usually are present when observing fatigue. It differs from dielectric hysteresis in that it can occur in the absence of any change in dynode voltage. Moreover, the gain hysteresis effect is most apparent after the detector has been left inactive in its "off" or "idle" mode, that is, left with the instrument light source turned off and with dynode voltage removed from the detector. As a result, the gain hysteresis effect is most prominent when the spectrophotometer is first turned "on" in preparation for measuring a sample, i.e., when dynode voltage is applied to the detector and the instrument light source is turned on allowing light therefrom to strike the detector cathode.

SUMMARY OF THE INVENTION

The present invention resides in a new and improved method and apparatus for minimizing gain hysteresis exhibited by a single beam spectrophotometer incorporating a photomultiplier detector. The present invention is simple and straightforward in configuration and operation and is readily adapted for incorporation in commercial spectrophotometers.

The environment of the present invention resides in a single beam spectrophotometer comprising a light source for illuminating a sample with light energy and a photomultiplier detector for receiving light energy from the sample and generating an output signal proportional thereto, the detector including a photoemissive cathode receiving incident light, a plurality of dynodes for multiplying electrons emitted from the cathode, and an anode at which an output current signal is derived. In this environment the invention is embodied in the combination comprising: (1) means conditioning the single beam spectrophotometer during normal instrument "on" or "operating" intervals for measuring a sample, the conditioning means including means for energizing the light source and for supplying dynode voltage to the photomultiplier detector; and (2) means operative during normal instrument "off" or "idle" intervals, when the instrument is not conditioned for measuring a sample, to illuminate the cathode of the detector and to supply dynode voltage to the detector dynodes. With this combination detector gain hysteresis is substantially reduced when the spectrophotometer is first conditioned for sample measurement during a subsequent "on" or "operating" interval.

In accordance with a further aspect of the invention the operative means energizes the spectrophotometer light source during such off or idle intervals to illuminate the detector cathode. Moreover, it has been discovered that the light source can be so operated at its full light output level or at a reduced level and provide sufficient illumination of the detector cathode to reduce detector gain hysteresis.

BRIEF DESCRIPTION OF THE FIGURE

FIG. 1 is a block diagram of a single beam spectrophotometer incorporating the present invention.

DESCRIPTION OF THE PREFERRED EMBODIMENT

FIG. 1 illustrates a single beam spectrophotometer indicated generally by numeral 10. The basic spectrophotometer system components of a form conventional in the art and will be described only to the extent necessary to set forth incorporation of the invention in the spectrophotometer. To this end, the spectrophotometer includes one or more light sources 12 light energy from which is directed along an optical path or axis 14 through a grating monochromator 16, through a filter changing mechanism 18, through a sample receiving compartment 20 and sample 22 therein, and thence to a photomultiplier detector 24. In the preferred embodiment the detector is an R928 multiplier manufactured and sold by Hamamatsu TV Co. Ltd.

Two light sources 12 are illustrated, one a white light tungsten incandescent lamp and the other, a deuterium lamp. A rotatable source mirror 26 is controlled so as to direct light from one or the other sources 12 along optical path 14.

Grating monochromator 16 includes a diffraction grating 28 whose position in the optical path is controlled in a conventional manner by motor 30 so as to control the wavelength of light energy exiting the monochromator along path 14.

Filter mechanism 18 is controlled by a conventional motor 32 so as to position any of various selectable filters in path 14 to attenuate or further control the light energy directed along optical path 14.

Light energy passed by the filter mechanism 18 is directed into sample compartment 20 and is intercepted by sample 22 therein. Light energy passed by the sample is in turn received by mirror 34 which directs the light toward the photo-emissive cathode of photomultiplier detector 24. The detector output current signal derived at the anode thereof is amplified by preamplifier 36 and is converted to digital form by A-to-D converter 38. The digital signal is then supplied to a data acquisition and control system 40.

System 40 is either a hard-wired controller or a programmable microcomputer well known in the art. Control signals are supplied by the control system over respective control lines 42, 44 and 46 for controlling the rotating source mirror 26, and motors 30 and 32. Moreover, system 40 supplies a control signal over line 48 causing high voltage supply 50 to supply dynode voltage to the photomultiplier dynodes over line 52 in a conventional manner. It is understood that the particular hardware arrangement of such a microcomputer is well known in the art and forms no part of the present invention. In general, however, such general purpose computers include a central processing unit, a program sequence of memory instructions (a read-only memory), an uncommitted block of usable memory (a read/write memory), and various input and output interfacing capabilities. Instructions can be executed from the read-only memory. Data can be transferred into or out of the read-only memory and into or out of the central processing unit. The central processing unit is configured to fetch and/or execute data and/or instructions to and/or from the memories and to the various input and output control devices. Programming such a computer for automated instrument operation and for coordinating information processing is straightforward and well established in the art.

In general, system 40 conditions the single beam spectrophotometer 10 in a conventional manner for operation during a normal "on" or "operating" interval in which a sample 22 is to be measured. To this end, system 40 energizes all spectrophotometer systems, subsystems and components in preparation for insertion of a sample into the sample compartment 20 and actual measurement thereof. When the sample measurements are completed, system 40 operates, in response to an internally generated signal or to an operator actuated "off" switch signal, to turn off the spectrophotometer and hence place it in an "off" or "idle" operating mode. In the off mode, the source 12 and detector 24 are inactivated by removing supply and dynode voltages therefrom, and, of course, sample measurements are not possible. The instrument is kept in the off mode until it is desired to be re-energized for a sample measurement. Typically an instrument is turned off at the end of a day and is kept in the off or idle mode at least overnight or for several days until it is to be used again. As indicated earlier, it has been discovered that single beam spectrophotometers exhibit serious gain hysteresis when turned on, i.e., when the detector 24 exposed to light and dynode voltage, after having been inactive in the off or idle mode.

In accordance with the present invention, system 40 comprises means operative during normal instrument "off" or "idle" intervals, when the instrument is not conditioned for measuring a sample, to illuminate the photomultiplier cathode and to supply dynode voltage to the detector dynodes. In this regard, when an off or idle command signal is received from an operator or from other instrument controls, control system 40 functions to energize light source 12 via line 54 and to energize the photomultiplier dynodes via line 48. In this manner, during the instrument off or idle interval, when sample measurement is not otherwise possible, the detector 24 is illuminated by light source 12 and receives dynode voltage from voltage source 50. It has been discovered that so illuminating and energizing the photomultiplier during its normal off or idle interval, substantially reduces the level of gain hysteresis exhibited when the instrument is again turned on for measuring a sample.

It has also been discovered that such offinterval illumination of the detector need not be at the full output level of source 10. Consequently, source 40 may be programmed to illuminate source 12, but at a reduced level, by appropriately inserting a resistor (not shown) in the supply voltage line connected to the source.

Moreover, while a preferred embodiment of the invention has been illustrated and described, modifications may be made therein without departing from the invention as defined in the appended claims.

What is claimed is:

1. A single beam spectrophotometer comprising:
   a light source for illuminating a sample with light energy;
   a photomultiplier detector for receiving light energy from the sample and generating an output signal proportional thereto, the photomultiplier including a photo-emissive cathode receiving incident light, a plurality of dynodes for multiplying electrons emitted by a cathode, and an anode at which the output current signal is derived;
   means conditioning the single beam spectrophotometer during instrument "on" or "operating" intervals for measuring the sample, said conditioning means including means for energizing the light source and for supplying dynode voltage to the photomultiplier dynode; and
   means operative during normal instrument "off" or "idle" intervals, when the instrument is not conditioned for measuring a sample, to illuminate the photomultiplier cathode and to supply dynode voltage to the photomultiplier dynode.

2. The single beam spectrophotometer of claim 1 wherein the operative means energizes said light source for illuminating the photomultiplier cathode during the "off" or "idle" intervals.

3. The single beam spectrophotometer of claim 2 wherein the operative means energizes said light source at a reduced light level than that at which it is energized during instrument "on" intervals.

* * * * *